United States Patent
Merot et al.

(10) Patent No.: US 10,300,195 B2
(45) Date of Patent: May 28, 2019

(54) AMBULATORY INFUSION DEVICES AND ASSOCIATED METHODS

(71) Applicant: Medallion Therapeutics, Inc., Valencia, CA (US)

(72) Inventors: Christian M. Merot, Ventura, CA (US); Pedrum Minaie, Burbank, CA (US)

(73) Assignee: Medallion Therapeutics, Inc., Santa Clarita, CA (US)

( * ) Notice: Subject to any disclaimer, the term of this patent is extended or adjusted under 35 U.S.C. 154(b) by 197 days.

(21) Appl. No.: 15/410,736

(22) Filed: Jan. 19, 2017

(65) Prior Publication Data

US 2017/0203031 A1 Jul. 20, 2017

Related U.S. Application Data

(60) Provisional application No. 62/281,065, filed on Jan. 20, 2016.

(51) Int. Cl.
*A61M 5/142* (2006.01)
*A61M 5/168* (2006.01)
(Continued)

(52) U.S. Cl.
CPC .... *A61M 5/14244* (2013.01); *A61M 5/14276* (2013.01); *A61M 5/14593* (2013.01);
(Continued)

(58) Field of Classification Search
CPC ........ A61M 5/142; A61M 2005/14208; A61M 5/1452; A61M 5/168; A61M 5/16804; A61M 5/16831; A61M 5/16877; A61M 5/16886; A61M 5/172; A61M 2205/50; A61M 2205/3334; A61M 2205/3341;
(Continued)

(56) References Cited

U.S. PATENT DOCUMENTS 3,926,056 A 12/1975 Brown
4,013,074 A 3/1977 Siposs
(Continued)

FOREIGN PATENT DOCUMENTS

DE 19642234 C1 4/1998
WO WO-96/27398 A1 9/1996
(Continued)

OTHER PUBLICATIONS

PCT International Search and Written Opinion dated May 11, 2017 for PCT App. Ser. No. PCT/US2017/014196.

*Primary Examiner* — Amber R Stiles
*Assistant Examiner* — Nicholas J Chidiac
(74) *Attorney, Agent, or Firm* — Henricks Slavin LLP (57) ABSTRACT

A method of operating an infusion device that includes the steps of actuating a fluid transfer device, which is configured to deliver a predetermined volume during each actuation, in accordance with a delivery profile that includes a plurality of fluid transfer device actuations, determining, based on sensed pressure, whether an actual volume delivered during a fluid transfer device actuation is the predetermined volume, and adjusting the number of actuations in the delivery profile in response to the actual volume delivered differing from the predetermined volume.

17 Claims, 9 Drawing Sheets

(51) Int. Cl.
*A61M 5/172* (2006.01)
*A61M 5/145* (2006.01)

(52) U.S. Cl.
CPC .... *A61M 5/16813* (2013.01); *A61M 5/16831* (2013.01); *A61M 5/16859* (2013.01); *A61M 2205/3331* (2013.01)

(58) Field of Classification Search
CPC ........ A61M 5/1723; A61M 2005/1726; A61M 2005/1405; A61M 2205/0216
See application file for complete search history.

(56) References Cited

U.S. PATENT DOCUMENTS

| | | | |
|---|---|---|---|
| 4,486,190 A | 12/1984 | Reinicke | |
| 4,530,696 A | 7/1985 | Bisera et al. | |
| 4,557,726 A | 12/1985 | Reinicke | |
| 4,636,150 A | 1/1987 | Falk et al. | |
| 4,690,673 A | 9/1987 | Bloomquist | |
| 4,714,462 A | 12/1987 | DiDomenico | |
| 4,718,893 A | 1/1988 | Dorman et al. | |
| 5,006,997 A | 4/1991 | Reich | |
| 5,190,522 A | 3/1993 | Wojcicki et al. | |
| 5,695,473 A | 12/1997 | Olsen | |
| 5,785,681 A | 7/1998 | Indravudh | |
| 5,888,242 A | 3/1999 | Antaki et al. | |
| 5,935,106 A | 8/1999 | Olsen | |
| 5,989,222 A | 11/1999 | Cole et al. | |
| 6,231,560 B1 | 5/2001 | Bui et al. | |
| 6,354,999 B1 | 3/2002 | Dgany et al. | |
| 6,423,029 B1 | 7/2002 | Elsberry | |
| 6,595,756 B2 | 7/2003 | Gray et al. | |
| 6,620,151 B2 | 9/2003 | Blischak et al. | |
| 6,942,636 B2 * | 9/2005 | Holst ................ | A61M 5/14224 604/19 |
| 7,022,116 B2 | 4/2006 | Morris | |
| 7,054,782 B2 | 5/2006 | Hartlaub | |
| 7,367,968 B2 | 5/2008 | Rosenberg et al. | |
| 7,402,154 B2 * | 7/2008 | Holst ................ | A61M 5/14224 604/153 |
| 9,429,452 B2 * | 8/2016 | Amiri ...................... | G01F 1/34 |
| 10,220,132 B2 * | 3/2019 | Patel ................ | A61M 5/14212 |
| 2004/0231432 A1 * | 11/2004 | Clark ................ | A61M 5/16813 73/861.52 |
| 2004/0260229 A1 | 12/2004 | Meir | |
| 2005/0038360 A1 | 2/2005 | Shertukde et al. | |
| 2005/0075624 A1 | 4/2005 | Miesel | |
| 2005/0090799 A1 | 4/2005 | Morris | |
| 2007/0191770 A1 | 8/2007 | Moberg et al. | |
| 2008/0021395 A1 | 1/2008 | Yodfat et al. | |
| 2008/0139996 A1 | 6/2008 | Bowman et al. | |
| 2008/0257412 A1 * | 10/2008 | Gordon ............. | A61M 5/16877 137/8 |
| 2009/0048562 A1 | 2/2009 | Falk et al. | |
| 2009/0221986 A1 | 9/2009 | Wang et al. | |
| 2010/0137842 A1 | 6/2010 | Gibson | |
| 2010/0145302 A1 * | 6/2010 | Cull .................... | A61M 1/0031 604/505 |
| 2012/0031497 A1 * | 2/2012 | Gordon ............. | A61M 5/16877 137/1 |
| 2012/0031503 A1 * | 2/2012 | Gordon ............. | A61M 5/16877 137/215 |
| 2012/0031513 A1 * | 2/2012 | Gordon ............. | A61M 5/16877 137/551 |
| 2012/0282111 A1 | 11/2012 | Nip et al. | |
| 2013/0211744 A1 * | 8/2013 | Amiri ...................... | G01F 1/34 702/47 |
| 2014/0094771 A1 | 4/2014 | Li et al. | |

FOREIGN PATENT DOCUMENTS

| | | |
|---|---|---|
| WO | WO-99/55225 A1 | 11/1999 |
| WO | WO-06/127508 A2 | 11/2006 |

* cited by examiner

AMBULATORY INFUSION DEVICES AND ASSOCIATED METHODS

CROSS-REFERENCE TO RELATED APPLICATIONS

This application claims the benefit of and priority to previously filed U.S. Provisional Patent Application Ser. No. 62/281,065, filed Jan. 20, 2016, which is entitled "Method For Detecting Volume Delivered in An Implantable Drug Pump Without A Flow Sensor" and incorporated herein by reference in its entirety.

BACKGROUND OF THE INVENTIONS

1. Field of Inventions

The present inventions relate generally to ambulatory infusion devices.

2. Description of the Related Art

Ambulatory infusion devices, such as implantable infusion devices and externally carried infusion devices, have been used to provide a patient with a medication or other substance (collectively "infusible substance") in accordance with a delivery profile that specifies one or more flow rates during the delivery profile cycle, and frequently include a reservoir and a fluid transfer device. The reservoir is used to store the infusible substance and is coupled to the fluid transfer device which is, in turn, connected to an outlet port. A catheter, which has at least one outlet at the target body region, may be connected to the outlet port. As such, infusible substance in the reservoir may be transferred from the reservoir to the target body region by way of the fluid transfer device and catheter. Some fluid transfer devices, such as those which include electromagnet pumps, are configured to deliver only a single (i.e., non-adjustable) volume during each actuation, while others are configured such that the volume delivered can be adjusted from one actuation to another.

One important aspect of an ambulatory infusion device is accuracy, i.e., whether or not the infusion device is actually delivering the volume specified by the delivery profile to the outlet port. In some implantable infusion devices, delivery accuracy can only be evaluated at the time of refill when the clinician is able to compare the expected delivery volume (based on the delivery profile) with actually delivered volume. Refills typically occur only once every three months. Given that the labeled accuracy of implantable infusion devices are frequently ±15%, attempts have been made to monitor actual delivery with the infusion device itself and to automatically compensate for actual delivery volume that deviates from the volume associated with the delivery profile. Although useful, the present inventors have determined that conventional methods and apparatus for monitoring delivery and responding to delivery inaccuracy are susceptible to improvement.

SUMMARY

A method of operating an infusion device in accordance with at least one of the present inventions includes the steps of actuating a fluid transfer device, which is configured to deliver a predetermined volume during each actuation, in accordance with a delivery profile that includes a plurality of fluid transfer device actuations, determining, based on sensed pressure, whether an actual volume delivered during a fluid transfer device actuation is the predetermined volume, and adjusting the number of actuations in the delivery profile in response to the actual volume delivered differing from the predetermined volume.

An infusion device in accordance with at least one of the present inventions an outlet port, a fluid transfer device configured to deliver a predetermined volume during each actuation thereof, a fluid path that operably connects the fluid transfer device to the outlet port, a pressure sensor associated with the fluid path, and means for actuating a fluid transfer device in accordance with a delivery profile that includes a plurality of fluid transfer device actuations, determining based on pressure sensed by the pressure sensor whether an actual volume delivered during a fluid transfer device actuation is the predetermined volume, and adjusting the number of actuations in the delivery profile in response to the actual volume delivered differing from the predetermined volume.

There are a variety of advantages associated with such methods and apparatus. For example, by simply adding or subtracting future actuations to correct volumetric inaccuracies, the present methods and apparatus and respond to delivery inaccuracies in a manner that is more efficient than conventional methods and apparatus.

BRIEF DESCRIPTION OF THE DRAWINGS

Detailed descriptions of exemplary embodiments will be made with reference to the accompanying drawings.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions. The present inventions have application in a wide variety of apparatus. One example is an electromagnet-pump-based fluid transfer device that may be employed in an implantable infusion device, and some of the present inventions are discussed in the context of electromagnet-pump-based fluid transfer devices and implantable infusion devices. The present inventions are not, however, limited to electromagnet-pump-based fluid transfer devices and implantable infusion devices and are instead also applicable to other fluid transfer devices and infusion devices that currently exist, or are yet to be developed. For example, the present inventions are applicable to fluid transfer devices with solenoid pumps or any other pump that delivers a known and non-adjustable volume into a compliant volume.

One example of an implantable infusion device that is configured to compensate for variations in pump stroke volume is generally represented by reference numeral 100 in FIGS. 1-4. As used herein, an "implantable infusion device" is a device that includes a reservoir and an outlet, and is sized, shaped and otherwise constructed (e.g. sealed) such that both the reservoir and outlet can be simultaneously carried within the patient's body. The exemplary infusion device 100 includes a housing 102 (e.g. a titanium housing) with a bottom portion 104, an internal wall 106, and a cover 108. An infusible substance (e.g. medication) may be stored in a reservoir 110 that is located within the housing bottom portion 104. The reservoir 110 may be replenished by way of a fill port 112 that extends from the reservoir, through the internal wall 106, to the cover 108. A hypodermic needle (not shown), which is configured to be pushed through the fill port 112, may be used to replenish the reservoir 110.

Figure 1:
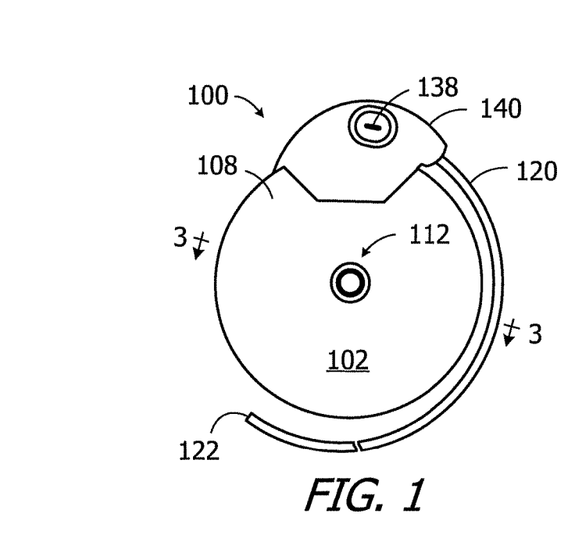
FIG. 1 is a plan view of an implantable infusion device in accordance with one embodiment of a present invention.
Figure 2:
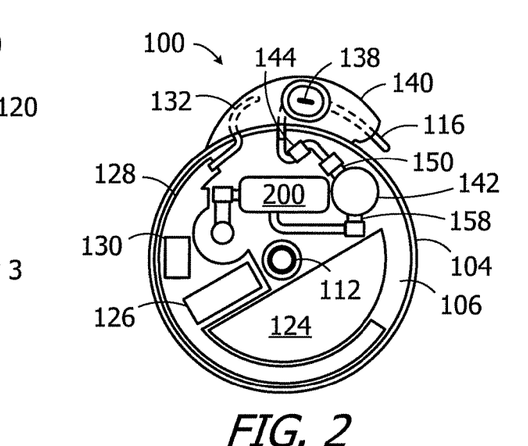
FIG. 2 is a plan view of the implantable infusion device illustrated in FIG. 1 with the cover removed.
Figure 3:
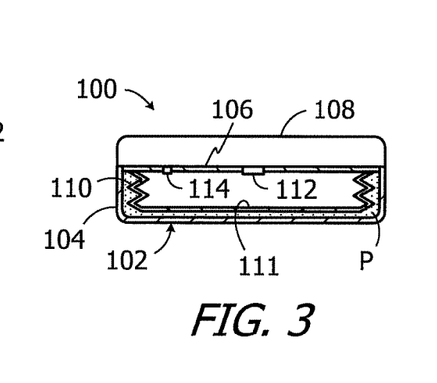
FIG. 3 is a partial section view taken along line 3-3 in FIG. 1.

A wide variety of reservoirs may be employed. In the illustrated embodiment, the reservoir 110 is in the form of a titanium bellows with an end wall 111 that is positioned within a sealed volume defined by the housing bottom portion 104 and internal wall 106. The remainder of the sealed volume is occupied by propellant P, which may be used to exert negative pressure on the reservoir 110. Other reservoirs that may be employed in the present infusion devices include reservoirs in which propellant exerts a positive pressure. Still other exemplary reservoirs include negative pressure reservoirs that employ a movable wall that is exposed to ambient pressure and is configured to exert a force that produces an interior pressure which is always negative with respect to the ambient pressure.

The exemplary ambulatory infusion device 100 illustrated in FIGS. 1-4 also includes a fluid transfer device 200, which is discussed in greater detail below with reference to FIGS. 6-10. The inlet of the fluid transfer device 200 is coupled to the interior of the reservoir 110 by a passageway 114 that is connected to an inlet tube associated with the fluid transfer device 200, while the outlet tube of the fluid transfer device is coupled to an outlet port 116 by a passageway 118 that defines a path from the fluid transfer device to the outlet port. Operation of the fluid transfer device 100 causes infusible substance to move from the reservoir 110 to the infusion device outlet port 116. A catheter 120 may be connected to the outlet port 116 so that the infusible substance passing through the outlet port will be delivered to a target body region in spaced relation to the infusion device 100 by way of the outlet(s) 122 at or near the end of the catheter.

Energy for the fluid transfer device 200, as well for other aspects of the exemplary infusion device 100, is provided by the battery 124 illustrated in FIG. 2. In the specific case of the fluid transfer device 100, the battery 124 is used to charge one or more capacitors 126, and is not directly connected to the fluid transfer device itself. The capacitor(s) 126 are connected to an electromagnet coil in the fluid transfer device 100, and disconnected from the battery 124, when the electromagnet coil is being energized, and are disconnected from the electromagnet coil and connected to the battery when the capacitor(s) are being recharged and/or when the fluid transfer device is at rest. The capacitor(s) 126 are carried on a board 128. A communication device 130, which is connected to an antenna 132, is carried on the same side of the board 128 as the capacitor(s) 126. The exemplary communication device 130 is an RF communication device. Other suitable communication devices include, but are not limited to, oscillating magnetic field communication devices, static magnetic field communication devices, optical communication devices, ultrasound communication devices and direct electrical communication devices.

A controller 134 (FIG. 4), such as a microprocessor, microcontroller or other control circuitry, is carried on the other side of the board 128. The controller 134 performs the function of controlling the operations of the infusion device 100 in accordance with instructions stored in memory 136 and/or provided by an external device (e.g. a remote control programmer) by way of the communication device 130. For example, the controller 134 may be used to control the fluid transfer device 100 to supply fluid to the patient in accordance with, for example, a stored basal delivery profile or a bolus delivery request. The controller 134 may also be used to monitor sensed pressure and to perform the analytical and corrective functions described below with reference to FIGS. 14 and 15.

Figure 4:
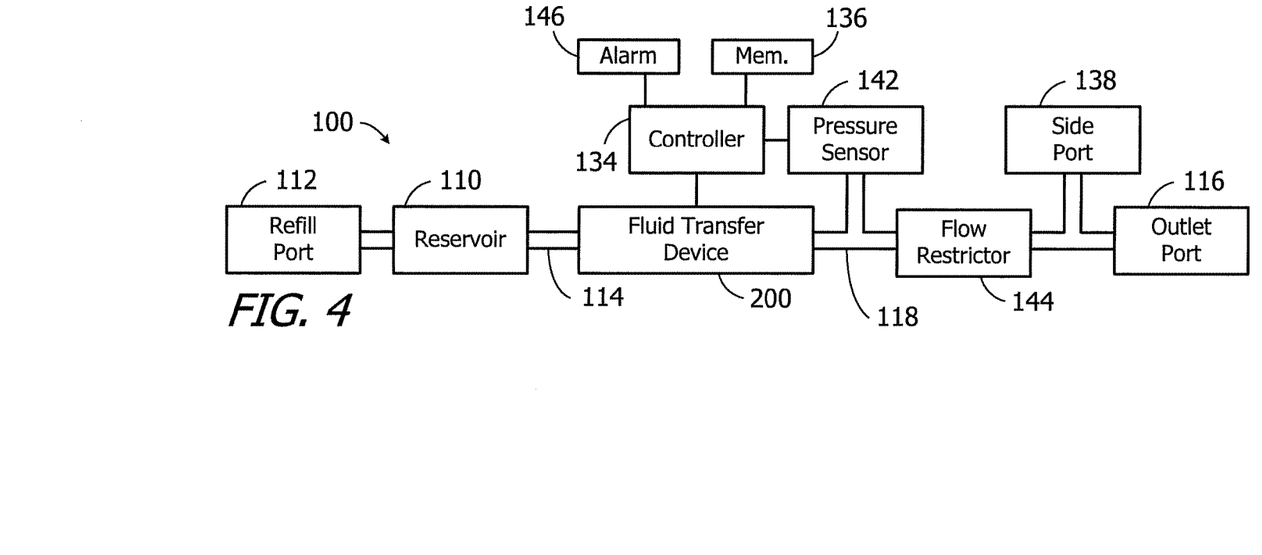
FIG. 4 is a block diagram of the implantable infusion device illustrated in FIGS. 1-3.

Referring to FIGS. 1, 2 and 4, the exemplary infusion device 100 is also provided with a side port 138 that is connected to the passageway 118 between the outlet of the fluid transfer device 200 and the outlet port 116. The side port 138 facilitates access to an implanted catheter 120, typically by way of a hypodermic needle. The outlet port 116, a portion of the passageway 118, the antenna 132 and the side port 138 are carried by a header assembly 140. The header assembly 140 is a molded, plastic structure that is secured to the housing 102. The housing 102 includes a small aperture through which portions of the passageway 118 are connected to one another, and a small aperture through which the antenna 132 is connected to the board 128.

The exemplary infusion device 100 illustrated in FIGS. 1-4 also includes a pressure sensor 142 and a flow restrictor 144 that are connected to the passageway 118 between the outlet of the fluid transfer device 200 and the outlet port 116. The fluid transfer device 200 drives fluid into the pressure sensor 142, which is a variable volume device, while the flow restrictor 144 impedes flow out of the pressure sensor so that the pressure spikes (and/or entire pressure profiles) associated with each actuation of the fluid transfer device can be accurately measured. The pressure sensor 142 is connected to the controller 134 and may be used to analyze a variety of aspects of the operation of the exemplary implantable infusion device 100. For example, pressure measurements may be used by the controller 134 to determine whether or not there is a blockage in the catheter 120 and whether or not the fluid transfer device 200 is functioning properly. The controller 134 may perform a variety of different functions in response to a determination that the fluid transfer device 200 is not functioning properly or a determination that the catheter 120 is blocked. For example, the controller 134 may actuate an audible alarm 146 that is located within the housing 102 in order to signal that the fluid transfer device 200 is not functioning properly or the catheter 120 is blocked. The controller 134 may also be used to the determine, based on the pressure sensed by the pressure sensor 142, the actual volume of fluid transferred during an actuation of the fluid transfer device 200 and to add or subtract future actuations to correct volumetric inaccuracies, in the manner described below with reference to FIGS. 14-15. To that end, exemplary infusion device 100 does not include a flow sensor.

Figure 5:
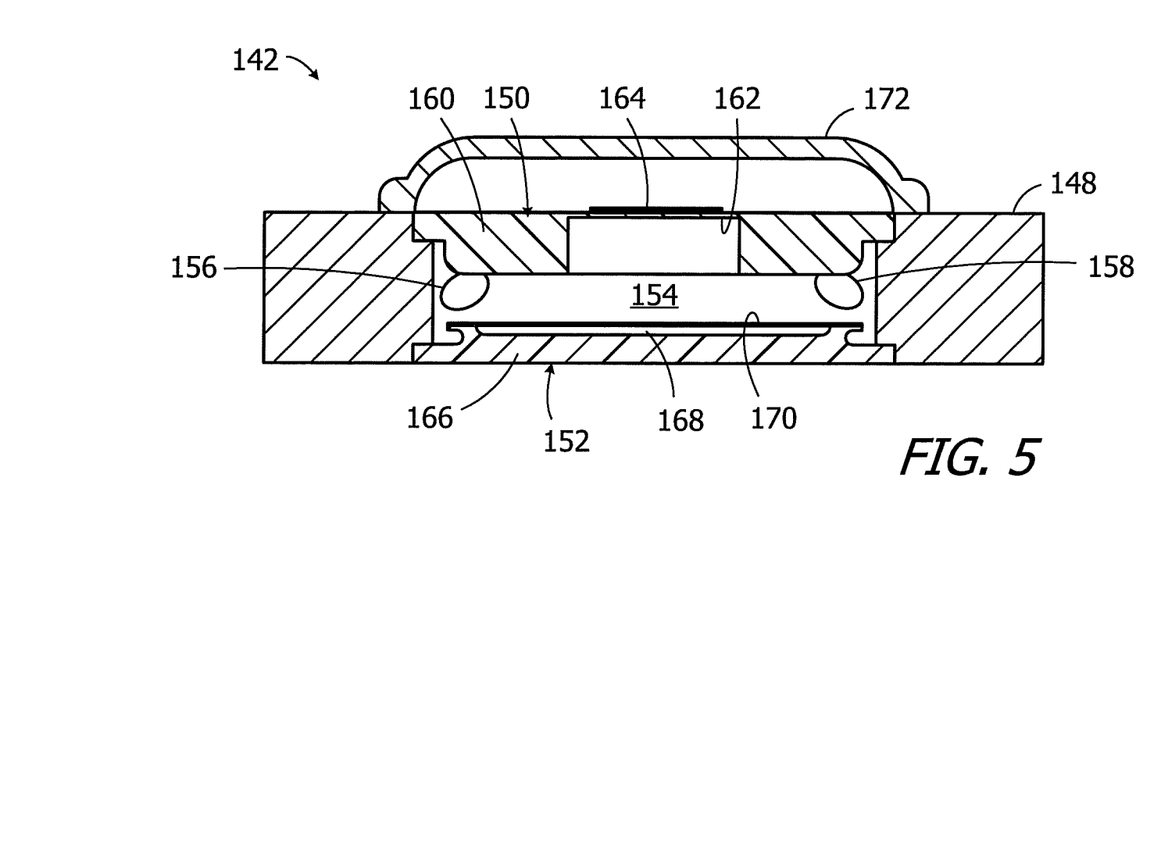
FIG. 5 is a section view of an exemplary pressure sensor.

Turning to FIGS. 2 and 5, the exemplary pressure sensor 142 includes a housing 148, a sensor apparatus 150, a fluid accommodation apparatus 152. The housing 148 includes a variable volume region 154, with an inlet 156 that is in fluid communication with the fluid transfer device outlet tube 290 (FIG. 6) and an outlet that is in fluid communication with the flow restrictor 144, which is located between the sensor apparatus 150 and the fluid accommodation apparatus 152. The sensor apparatus 150 includes a base 160, a compliant diaphragm 162 (which is circular in the illustrated implementation), and a strain gauge 164. The fluid accommodation apparatus 152 includes a base 166 that defines an accommodation volume 168 as well as a compliant diaphragm 170 that is positioned over the accommodation volume. A cap 172 covers the sensor apparatus 150. The pressure sensor 142 has a known (and calibrated) compliance value (e.g., 0.125 microliters/psi), which is a function of the compliance of diaphragms 162 and 170, that can be monitored with the strain gauge 164. Here, a stroke volume of 0.25 microliters will result in a 2 psi pressure increase. Each stroke can be evaluated based on measured pressure in the manner described below with reference to FIGS. 14-15. The compliance of the diaphragms 162 and 170 and the presence of the flow restrictor 144 facilitate rapid actuation of the fluid transfer device and the relative slow delivery of the fluid to the outlet port 116.

One example of a fluid transfer device is illustrated in FIGS. 6-10. The exemplary fluid transfer device, which is generally represented by reference numeral 200, includes an electromagnet pump. Actuation of the fluid transfer device 200 results in a single pump stroke from the electromagnet pump, and the fluid transfer device is configured to deliver a predetermined volume per stroke (e.g., 0.25 microliters/stroke in the illustrated embodiment) when operating properly at a given ambient pressure. The volume per stroke is a function of the piston diameter and stroke length. The electromagnet pump is not configured to selectively deliver partial strokes, and the fluid transfer device 200 is not configured to be selectively partially actuated. In other words, although the volume per stroke may vary due to inaccuracy in the system (e.g., minor variation in the speed at which the valves open and close) or variations in ambient pressure, the fluid transfer device 200 has a fixed delivery volume and the volume per stroke is not adjustable. The electromagnet pump may be referred to as a "fixed displacement electromagnet pump."

Figure 6:
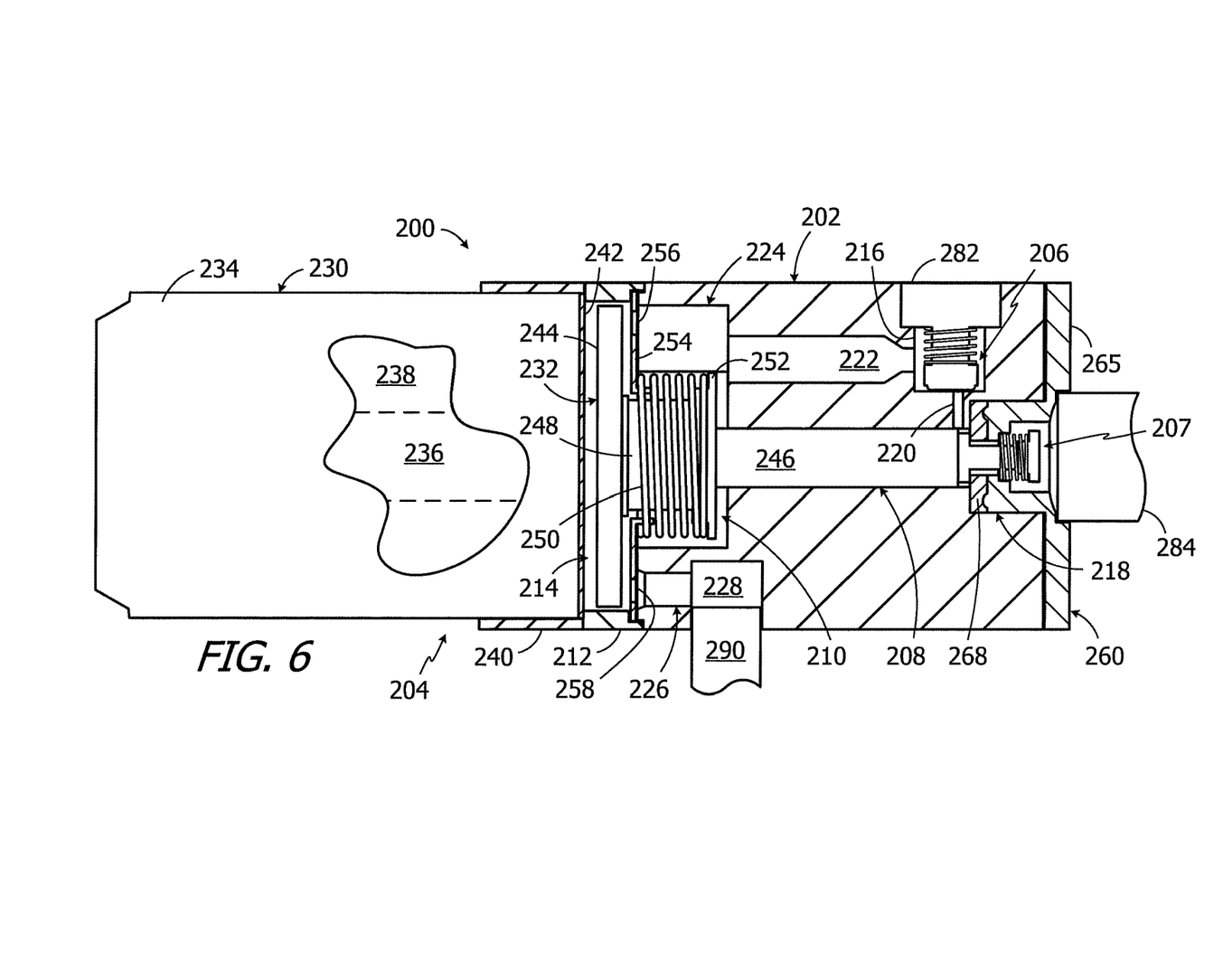
FIG. 6 is a side, partial section view of a fluid transfer device in accordance with one embodiment a present invention.

Referring first to FIG. 6, the exemplary fluid transfer device 200 includes a housing 202, an electromagnet pump 204, a bypass valve 206 and a main check valve 207. The valves 206 and 207 are in fluidic communication with the pump 204. The housing 202 in the exemplary fluid transfer device 200 is a generally solid, cylindrical structure with various open regions. The open regions accommodate portions of structures, such as the electromagnet pump 204, bypass valve 206, main check valve 207, and also define a fluid flow path. More specifically, the housing 202 includes a piston bore 208 and a hub recess 210 that respectively receive the electromagnet pump armature piston 246 and armature hub 248 (discussed below). A weld ring 212, which is secured to the end of the housing 202 opposite the main check valve 207, defines a pole recess 214 for the armature pole 244 (discussed below). A pair of valve recesses 216 and 218 for the bypass valve 206 and main check valve 207 are also provided. With respect to the fluid flow path, the housing 202 includes an orifice 220 that extends from the piston bore 208 to the bypass valve recess 216, a bypass fluid chamber 222, fluid passages 224 and 226, and an outlet recess 228.

Turning to the pump portion of the exemplary fluid transfer device 200, the electromagnet pump 204 includes an electromagnet 230 and an armature 232. The electromagnet 230, which is carried within in a case 234, includes a core 236 and a coil 238. The case 234 and core 236 are made from a magnetic material. The coil 238 consists of a wire or other conductor that is wound around the core 236. The coil 238 may be insulated from the case 234 by electrically non-conductive spacers (not shown), which center the coil within the case, or through the use of potting compound or encapsulant material between the case and the coil. The electromagnet case 234 is secured to the housing 202 in the exemplary fluid transfer device 200 through the use of the aforementioned weld ring 212 on the housing and a weld ring 240 on the case. A barrier 242 separates the pole recess 214, which will ultimately be filled with fluid, from the electromagnet 230.

The armature 232 in the illustrated embodiment is positioned within a fluid containing region of the housing that is defined by the piston bore 208, the hub recess 210 and the pole recess 214. The exemplary armature 232 consists of a pole 244 formed from a magnetic material (e.g. magnetic steel), which is located within the pole recess 214 such that it will be magnetically attracted to the electromagnet 230 when the electromagnet is actuated, and a cylindrically-shaped piston 246 that extends from the pole and through the piston bore 208 to the main check valve 207. A hub 248 is located within the hub recess 210 and is used to secure the pole 244 to the piston 246. A main spring 250 biases the armature 232 to the "rest" position illustrated in FIG. 6. The main spring 250 is compressed between a spring retainer 252 on the hub 248 and a spring retainer plate 254. The spring retainer plate 254, which is held in place by the housing 202 and the weld ring 212, includes an inlet opening 256 that allows fluid to pass from the fluid passage 224 to the pole recess 214 and an outlet opening 258 that allows fluid to pass from the pole recess to the fluid passage 226.

Figure 7:
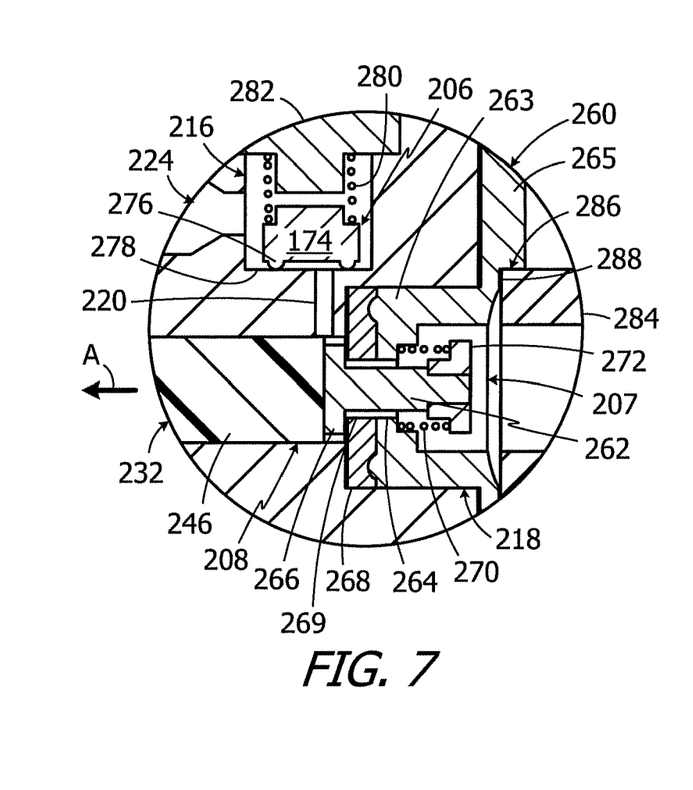
FIGS. 7-10 are section views showing the fluid transfer device illustrated in FIG. 6 in various states.

Turning to FIG. 7, the main check valve 207 includes a housing 260, which may be positioned within the valve recess 218 and secured to the housing 202, and a valve element (or "plunger") 262 that is movable relative to the housing 260. The exemplary housing 260 has a generally cylindrical fluid flow portion 263, with a fluid lumen 264 that is opened and closed by the valve element 262, and a mounting portion 265 that is used to secure the main check valve 207 to a fluid transfer device or other structure. The valve element 262 includes a head 266 that abuts an elastomeric valve seat 268 when the main check valve 207 is in the closed state illustrated in FIG. 7. The shaft portion of the valve element 262 passes through an opening 269 in the valve seat 268. The valve element 262 is biased to the closed position by a spring 270 (e.g. a coil spring) or other suitable biasing device. One end of the spring 270 abuts the housing 260 and the other end abuts a spring retainer 272 that is secured to the valve element 262. The exemplary valve seat 268 may have a main portion and a seal portion formed from material that is less tacky that the main portion, as is discussed in U.S. Pat. No. 8,251,960, which is incorporated herein by reference.

The exemplary bypass valve 206 includes a valve element 274 with an integral sealing ring 276. The sealing ring 276, which has a semi-circular cross-sectional shape, engages the wall (or "seat") 278 that defines the end of the valve recess 216 and surrounds the orifice 220 when in the closed position illustrated in FIG. 7. The valve element 274 is biased to the closed position by a spring 280. One end of the spring 280 abuts the valve element 274, while the other end abuts a plug 282 that may be secured to housing 202 to maintain the bypass valve 206 within the valve recess 216. The plug 282 also forms a fluid tight seal which prevents fluid from escaping from the housing 202 by way of the valve recess 216.

Fluid may be supplied to the exemplary fluid transfer device 200 illustrated in FIG. 6 by way of an inlet tube 284. To that end, and referring to FIG. 7, the main check valve housing 260 includes a recess 286, with a shoulder 288, that receives the inlet tube 284. A filter (not shown) may be positioned within the recess 286 between the inlet tube 284 and the shoulder 288. The recess 286 and shoulder 288 may, alternatively, be associated with the fluid flow portion 263, or with both the fluid flow portion and the mounting portion 265, in other implementations of the main check valve 207. Fluid exits the fluid transfer device 200 by way of an outlet tube 290 (FIG. 6) that is received within the outlet recess 228 in the housing 202.

The exemplary fluid transfer device 200 operates as follows. Referring first to FIGS. 6 and 7, the fluid transfer device 200 is shown here in the "rest" state. The armature 232 is in the rest position, the electromagnet 230 is not energized, and the bypass valve 206 and main check valve 207 are both closed. Under normal operating conditions, there will be no flow through the fluid transfer device 200 when the fluid transfer device is in the rest state and the valves 206 and 207 are closed.

The exemplary fluid transfer device 200 is actuated by connecting the coil 238 in the electromagnet 230 to an energy source (e.g. one or more capacitors that are being fired). The resulting magnetic field is directed through the core 236 and into, as well as through, the armature pole 244. The armature pole 244 is attracted to the core 236 by the magnetic field. The intensity of the magnetic field grows as current continues to flow through the coil 238. When the intensity reaches a level sufficient to overcome the biasing force of the main spring 250, the armature 232 will be pulled rapidly in the direction of arrow A (FIG. 7) until the armature pole 244 reaches the barrier 242. Such movement may take approximately 1 millisecond. The armature piston 246 and hub 248 will move with armature pole 244 and compress the main spring 250. This is also the time at which fluid exits the fluid transfer device 200 by way of the passage 226 and the outlet tube 290.

Figure 8:
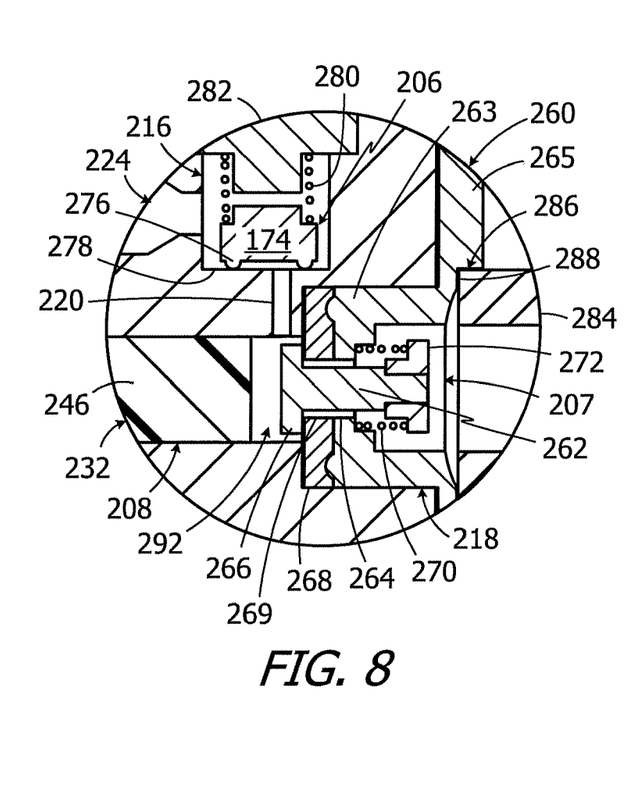
Figure 9:
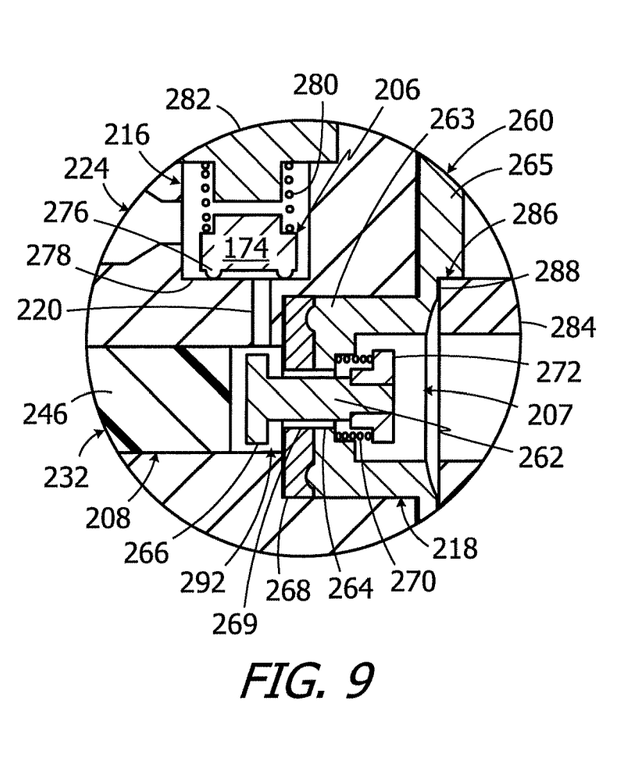
Figure 10:
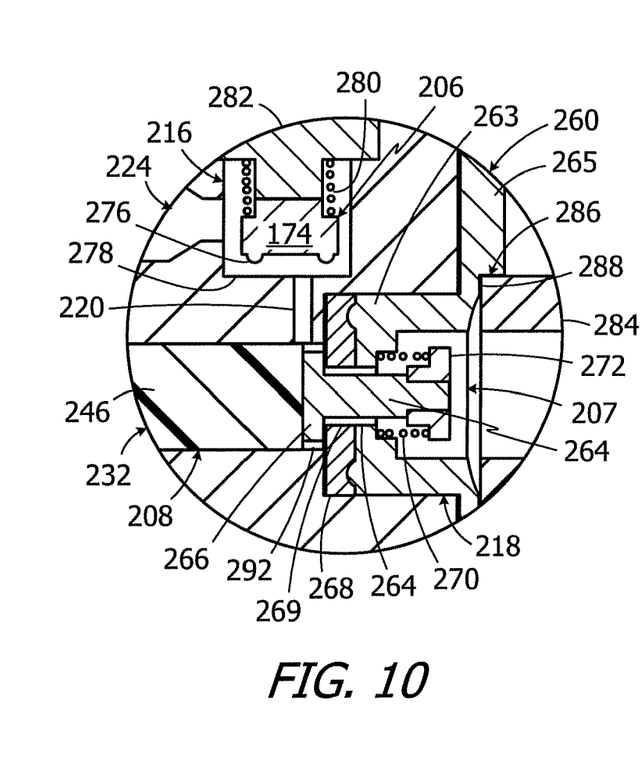

Movement of the armature piston 246 from the position illustrated in FIG. 7 to the position illustrated in FIG. 8 results in a decrease in pressure in the pump chamber 292, i.e. the volume within the piston bore 208 between the armature piston 246 and the valve seat 268. The coil will continue to be energized for a brief time (e.g. one to a few milliseconds) in order to hold the armature piston 246 in the location illustrated in FIG. 8. The reduction in pressure within the pump chamber 292 will open the main check valve 207 by overcoming the biasing force of the spring 270 and move valve element 262 to the position illustrated in FIG. 9. As a result, the valve head 266 will move away from the valve seat 268 and fluid will flow into the pump chamber 292. The main check valve 207 will close, due to the force exerted by spring 270 on valve element 262, once the pressure within pump chamber 292 is equal to pressure at the inlet tube 284. However, because the coil 238 continues to be energized, the armature 232 will remain in the position illustrated in FIGS. 8 and 9 as fluid flows into the pump chamber 292 and the main check valve 207 closes.

Immediately after the main check valve 207 closes, the coil 238 will be disconnected from the energy source and the magnetic field established by the electromagnet 230 will decay until it can no longer overcome the force exerted on the armature 232 by the main spring 250. The armature 232 will then move back to the position illustrated in FIGS. 7 and 10. The associated increase in pressure within the pump chamber 292 is sufficient to open the bypass valve 206 by overcoming the biasing force of the spring 280 and moving the valve element 274 to the position illustrated in FIG. 10. The increase in pressure within the pump chamber 292, coupled with movement of the valve element away from the wall 278, results in the fluid flowing through the orifice 220 to the fluid chamber 222. The flow of fluid will cause the pressure in the orifice 220 and the fluid chamber 222 to equalize. At this point, the bypass valve 206 will close, due to the force exerted by spring 280 on the valve element 274, thereby returning the exemplary fluid transfer device 200 to the rest state illustrated in FIGS. 6 and 7.

Figure 11:
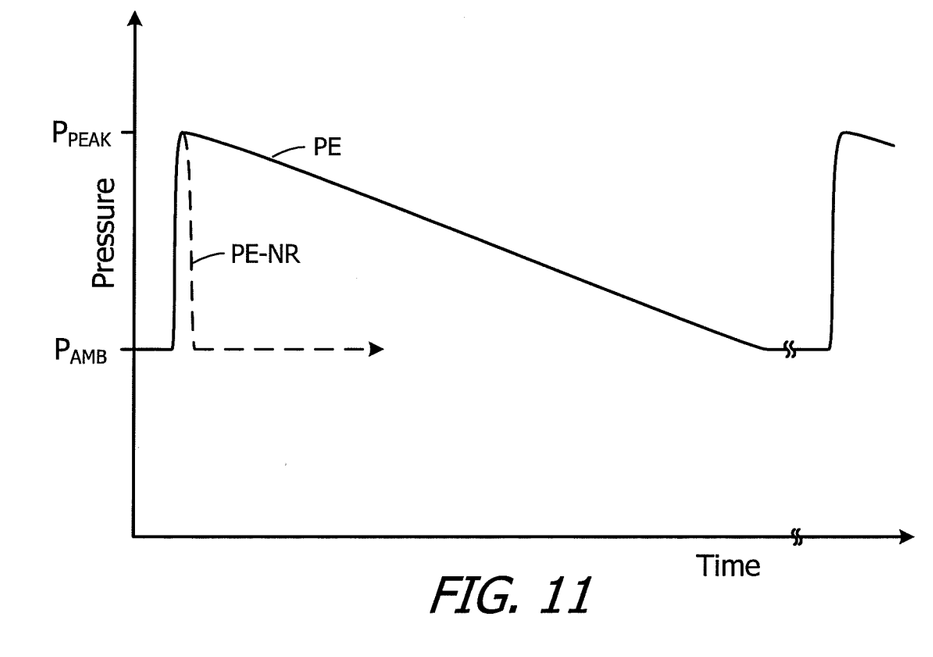
FIG. 11 is a graph illustrating a pressure measurement.

The pressure sensed by the pressure sensor 142, before, during and after an accurate actuation of the fluid transfer device 200 (and the associated pump stroke), i.e., an actuation that results in the predetermined volume per stroke (e.g., 0.25 microliters/stroke), is illustrated in FIG. 11. Prior to the actuation, the pressure measured by the pressure sensor 142 will be the ambient pressure $P_{AMB}$ as it exists in the catheter. A driving voltage is applied to the coil 238 when the fluid transfer device 200 is actuated, and the resulting magnetic field causes the piston 246 to move in the manner described above with reference to FIGS. 7 and 8. Fluid simultaneously exits the fluid transfer device 200, by way of the passage 226 and the outlet tube 290, and enters the pressure sensor 142. The pressure measured by the pressure sensor 142 immediately increases to the peak pressure $P_{PEAK}$ as the fluid enters the pressure sensor (and displaces the diaphragm by an amount corresponding to the stroke volume). The presence of the flow restrictor 144 allows the peak pressure $P_{PEAK}$ to be accurately measured because the pressure within the pressure sensor 142 rises quickly and then decays slowly to ambient pressure $P_{AMB}$ as shown by pressure event PE. In some instances, the pumps stroke occurs approximately 1 millisecond after capacitor connected to coil and takes approximately 1 millisecond, while the pressure decay back down to ambient pressure $P_{AMB}$ may take approximately 500 milliseconds due to flow restrictor 144. For purposes of comparison, the pressure within the pressure sensor 142 would almost immediately return to ambient pressure $P_{AMB}$ as shown by pressure event PE-NR.

Figure 12:
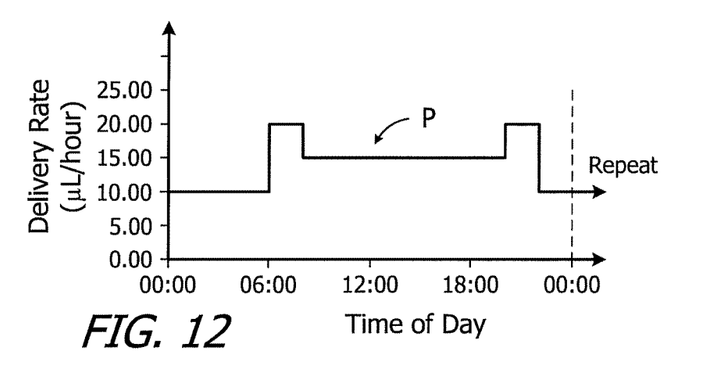
FIG. 12 is a graphical illustration of one example of a delivery profile.
Figure 13:
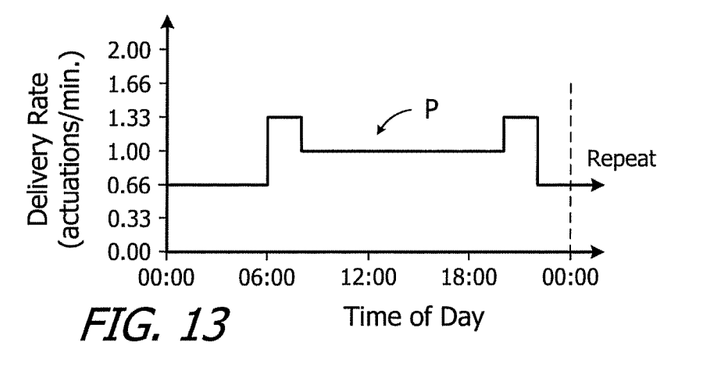
FIG. 13 is a graphical illustration of one example of a delivery profile.

The fluid transfer device 200 may be actuated in accordance with a delivery profile such as that illustrated in FIG. 12. Exemplary profile P, which has a twenty-four hour cycle time and may be expressed in terms of the volume delivered per hour as illustrated in FIG. 12, specifies that the infusible substance is to be delivered at a rate of 10 microliters/hour (µL/hour) from 00:00 to 06:00 hours, at a rate of 20 µL/hour from 06:00 to 08:00, at a rate of 15 µL/hour from 08:00 to 20:00, at a rate of 20 µL/hour from 20:00 to 22:00, and at a rate of 10 µL/hour from 22:00 to 24:00. Each actuation is a pump stroke that takes about 1-3 milliseconds to complete and results in the delivery of 0.25 µL of infusible substance to the pressure sensor 144 and, ultimately, to the catheter 120. When expressed in terms of actuations per minute in the manner illustrated in FIG. 13, the exemplary profile P specifies that the infusible substance is to be delivered at a rate of 0.66 actuations/minute from 00:00 to 06:00 hours, at a rate of 1.33 actuations/minute from 06:00 to 08:00, at a rate of 1.0 actuation/minute from 08:00 to 20:00, at a rate of 1.33 actuations/minute from 20:00 to 22:00, and at a rate of 0.66 actuations/minute from 22:00 to 24:00. As discussed below, the actual volume of fluid transferred during an actuation of the fluid transfer device 200 may be monitored, and actuations may be added or subtracted to correct monitored volumetric inaccuracies.

Figure 14:
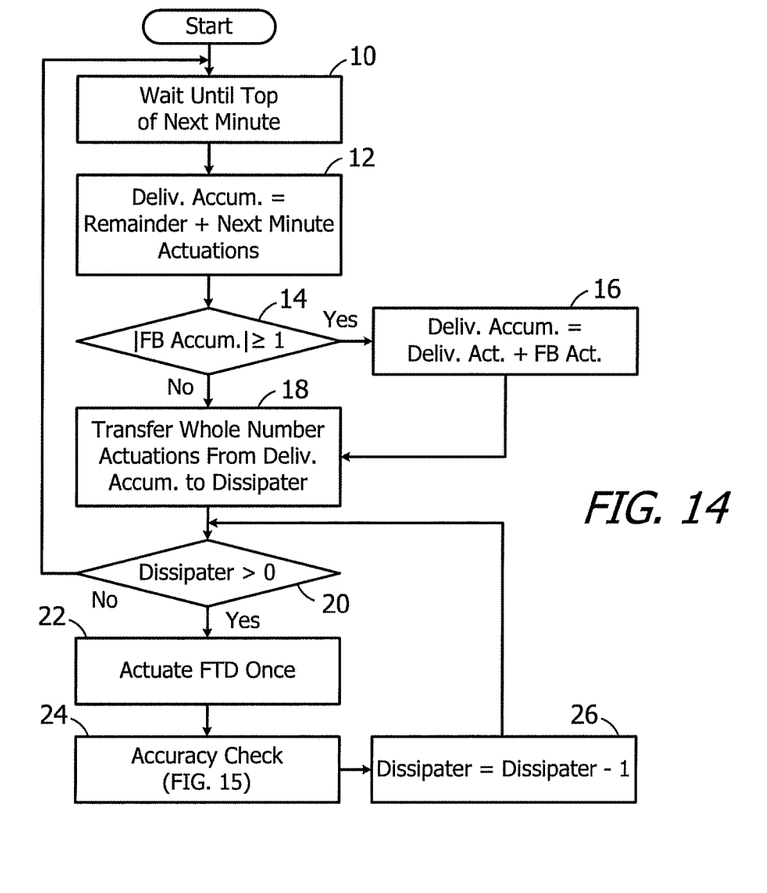
FIG. 14 is a flow chart in accordance with one embodiment of a present invention.

One example of a control method that may be employed by the implantable medical device controller 136 to execute a stored delivery profile, such as delivery profile P, is illustrated in FIG. 14. The control method actuates the associated fluid transfer device 200, when appropriate, at the top (i.e. beginning) of each minute. If, for example, two pump strokes or other fluid transfer device actuations are required per minute to maintain the requisite flow rate, those actuations will occur at the top of each minute. Accordingly, the first step in the exemplary method is to wait until the top of the minute to proceed (Step 10). The second step is to add the actuations associated with this minute to a remainder, if any, in a delivery accumulator, which is a delivery stroke counter in memory 136 (Step 12). If, for example, the rate associated with the minute was 1.33 actuations/minute, then 1.33 actuations would be added to the accumulator. Next, if the absolute value of the feedback accumulator (which is a stroke counter in memory 136 that is used to track delivery inaccuracy in the manner described below with reference to FIG. 15) is greater than or equal to 1 (Step 14) than the whole number of actuations in the feedback accumulator is added to (or subtracted from) the delivery accumulator (Step 16), thereby adjusting the number of actuations in the delivery profile. For example, if 1.02 actuations were in the feedback accumulator, then 1 actuation would be transferred to the delivery accumulator and there would be a remainder of 0.02 actuations in the feedback accumulator. If, on the other hand, −1.08 actuations were in the feedback accumulator, then −1 actuation would be transferred to the delivery accumulator and there would be a remainder of −0.08 actuations in the feedback accumulator. In this implementation, nothing is added to the delivery accumulator when the absolute value of the feedback accumulator is less than 1. In either case, the whole number of actuations in the delivery accumulator is transferred to a dissipater (Step 18). The fluid transfer device 200 is then actuated once, and the dissipater (which is a stroke counter in memory 136) is decremented by one actuation so long as there are actuations in the dissipater (Steps 20, 22 and 26). A pressure based accuracy check (Step 24) is also associated with each actuation.

Figure 15:
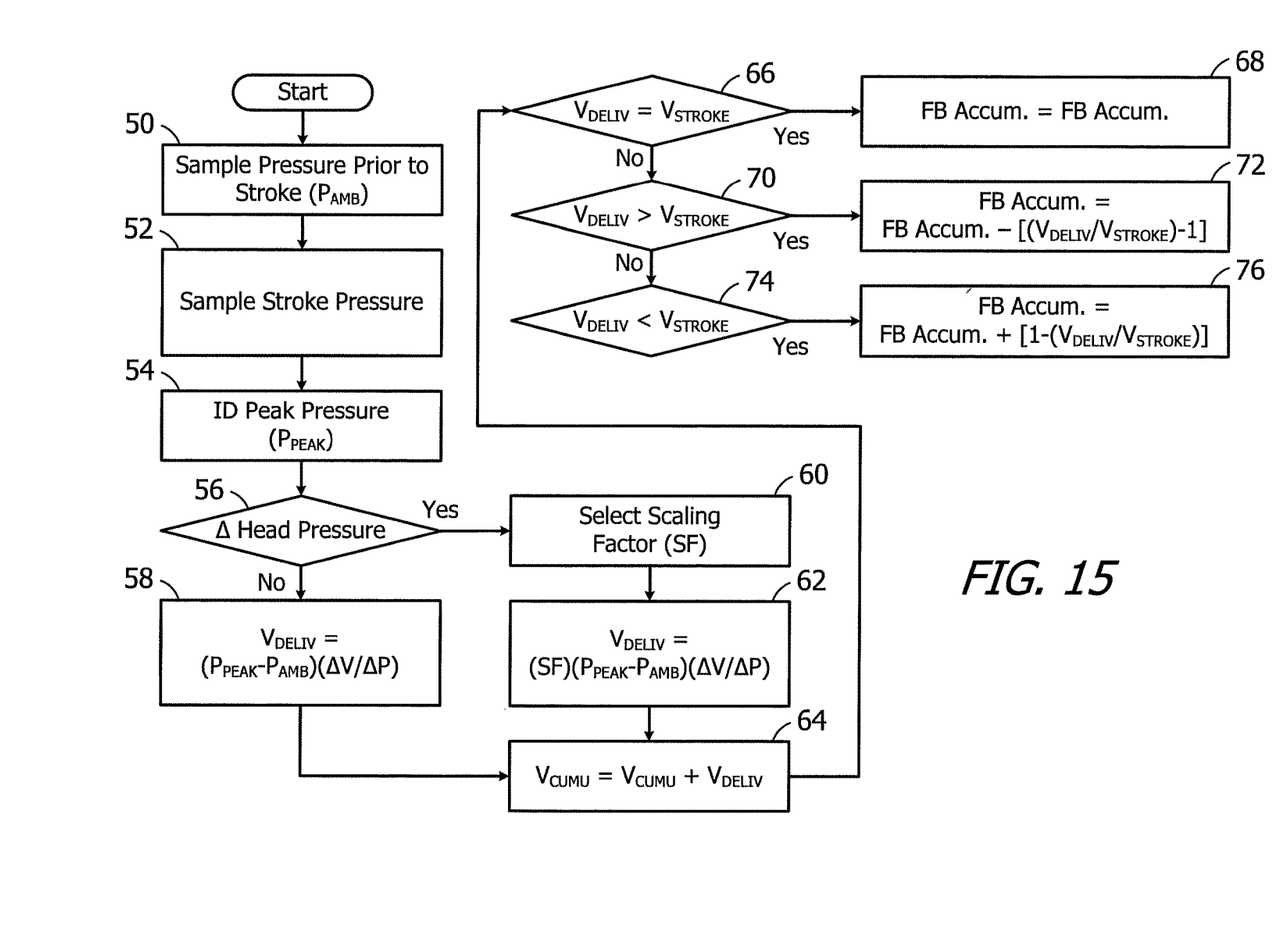
FIG. 15 is a flow chart in accordance with one embodiment of a present invention.

Turning to FIG. 15, one exemplary pressure-based method of determining whether an actual stroke volume delivered $V_{DELIV}$ is in fact the predetermined stroke volume $V_{STROKE}$, and then compensating for actual stroke volumes that deviate from the predetermined stroke volume, involves sensing ambient pressure $P_{AMB}$ with the pressure sensor 142 prior to the actuation of the fluid transfer device 200, sensing pressure during the pump stroke, and identifying the peak pressure $P_{PEAK}$ (Steps 50-54). The frequency at which the pressure sensor is sampled may be relatively high, e.g., 10 kHz, in order to insure that the peak pressure $P_{PEAK}$ is not missed. The effect of changes in head pressure, which may be due to changes in ambient pressure and catheter issues, is also taken into account. In particular, if the ambient pressure $P_{AMB}$ is equal to the expected head pressure (14.7 psi), then the stroke volume delivered $V_{DELIV}$ calculation may proceed (Step 56) without any adjustment based on the head pressure. Here, the actual stroke volume delivered $V_{DELIV}$ is equal to the magnitude of the pressure spike associated with the pump stroke ($P_{PEAK}-P_{AMB}$) times the compliance value $\Delta P/\Delta V$ of the pressure sensor diaphragm (Step 58). For example, when the compliance value is 0.125 microliters/psi, a 2 psi pressure spike would be indicative 0.25 micro- liter actual stroke volume. Alternatively, in those instances where head pressure is different than the expected head pressure, a scaling factor SF may be applied (Steps 60 and 62) to normalize the $V_{DELIV}$ calculation. The scaling factors SF are experimentally derived values that are stored in a look-up table. The applied scaling factor SF is selected from the look-up table based on the magnitude of the change in head pressure. The scaling factor SF will be greater than one when the there is an increase in head pressure, and less than one when there is a decrease in head pressure.

In some embodiments, the cumulative actual volume delivered $V_{CUMU}$ may also be calculated (Step 64), stored, and reported in response to a query from a remote control programmer or other device. The cumulative actual volume delivered $V_{CUMU}$ may be associated with any desired period, e.g., the cumulative actual volume delivered since the last refill, and may be reset to zero as desired to restart the cumulative delivery tracking period.

After the actual stroke volume delivered $V_{DELIV}$ has been calculated (Step 58 or 62), it is compared to the predetermined stroke volume $V_{STROKE}$ (Step 66) and, if the actual stroke volume delivered $V_{DELIV}$ is equal to the predetermined stroke volume $V_{STROKE}$, no changes are made to the feedback accumulator (Step 68). In those instances where the actual stroke volume delivered $V_{DELIV}$ is greater than the predetermined stroke volume $V_{STROKE}$, then the feedback accumulator is reduced by the amount of the over-delivery (Steps 70 and 72). The amount may be expressed in pump strokes or other actuation equivalents that correspond to the volumetric differential. For example, in those instances where the predetermined stroke volume $V_{STROKE}$ is 0.25 microliters and the actual stroke volume delivered $V_{DELIV}$ is 0.275 microliters (a 10% difference), then the feedback accumulator will be decreased by 0.1 strokes. Conversely, the feedback accumulator will be increased by the amount of the under-delivery in those instances where the actual stroke volume delivered $V_{DELIV}$ is less than the predetermined volume $V_{STROKE}$ (Steps 74 and 76). Accordingly, the feedback accumulator may store a positive value or a negative value.

As discussed above with reference to FIG. 14, the value of the feedback accumulator may be used to add or subtract pump strokes (Steps 14 and 16) to a delivery profile in order to correct monitored volumetric inaccuracies. In the illustrated implementation, the whole number of actuations in the feedback accumulator (which may be a positive or negative number) is added to the delivery accumulator and there would be a remainder actuations (with an absolute value less than 1) in the feedback accumulator. In other implementations, any and all actuations in the feedback accumulator (e.g., 1.02 actuations or −0.3 actuations) may be added to, or subtracted from, the delivery accumulator because the next step (Step 18) limits the number of strokes transferred from the delivery accumulator to the dissipater to whole numbers.

It should also be noted that the actual stroke volume delivered $V_{DELIV}$ determination may be based on aspects of the pressure profile (e.g., the profile illustrated in FIG. 11) other than the pressure spike. By way of example, but not limitation, the entire pressure profile can be integrated and calibrated to the actual stroke volume delivered. Alternatively, a Riemann sum approximation of the pressure profile may be employed.

Although the inventions disclosed herein have been described in terms of the preferred embodiments above, numerous modifications and/or additions to the above-described preferred embodiments would be readily apparent to one skilled in the art. By way of example, but not limitation, structures that perform the respective functions of the sensor apparatus 150 and fluid accommodation apparatus 152 may be located is separate housings and connected to the path defined by the passageway 118 (e.g., with the sensing function being performed downstream from the accommodation function). The present inventions also have application in infusion devices that include multiple reservoirs and/or outlets. Moreover, the inventions include any and all combinations of the elements from the various embodiments disclosed in the specification. It is intended that the scope of the present inventions extend to all such modifications and/or additions and that the scope of the present inventions is limited solely by the claims set forth below.

We claim:

1. A method of operating an infusion device, comprising the steps of:
   actuating a fluid transfer device, which is configured to deliver a predetermined volume during each actuation, in accordance with a delivery profile that includes a plurality of fluid transfer device actuations;
   determining whether an actual volume delivered during a fluid transfer device actuation is the predetermined volume by sensing pressure, at a single location with a single pressure sensor that is located upstream of a flow restrictor and that has a compliant diaphragm, a compliance value and a sensor apparatus located in spaced relation to the compliant diaphragm, and determining the magnitude of the of a pressure spike associated with the fluid transfer device actuation and multiplying the magnitude of the pressure spike by the compliance value; and
   adjusting the number of actuations in the delivery profile in response to the actual volume delivered differing from the predetermined volume.

2. A method as claimed in claim 1, wherein
   the fluid transfer device includes an electromagnet pump; and
   the actuation of the fluid transfer device includes a single pump stroke that creates a pressure spike.

3. A method as claimed in claim 1, wherein
   determining the magnitude of the pressure spike comprises sampling pressure sensed by the pressure sensor before and during the single pump stroke.

4. A method as claimed in claim 3, wherein
   determining the magnitude of the pressure spike comprises using a scaling factor to adjust for changes in head pressure.

5. A method as claimed in claim 1, wherein
   adjusting the number of actuations in the delivery profile comprises adding an actuation equivalent of an over-delivery volume to a feedback accumulator in response to the actual volume delivered being greater than the predetermined volume.

6. A method as claimed in claim 5, wherein
   adjusting the number of actuations in the delivery profile comprises subtracting an actuation equivalent of an under-delivery volume from the feedback accumulator in response to the actual volume delivered being less than the predetermined volume.

7. A method as claimed in claim 6, wherein
   actuating the fluid transfer device in accordance with the delivery profile includes storing the number of actuations in a delivery accumulator; and
   adjusting the number of actuations in the delivery profile comprises adding the actuation equivalent in the feedback accumulator to the delivery accumulator.

8. A method as claimed in claim 7, wherein
   adding the actuation equivalent in the feedback accumulator to the delivery accumulator comprises adding a whole number actuation equivalent to the delivery accumulator.

9. A method as claimed in claim 7, wherein
   the fluid transfer device comprises a fixed displacement fluid transfer device.

10. A method as claimed in claim 1, wherein
    the compliant diaphragm defines a first compliant diaphragm; and
    the sensor apparatus includes a second compliant diaphragm and a strain gauge.

11. A method as claimed in claim 10, wherein
    the compliance value is a function of the compliance of the first and second compliant diaphragms.

12. An ambulatory infusion device, comprising:
    an outlet port;
    a fluid transfer device configured to deliver a predetermined volume during each actuation thereof;
    a fluid path that operably connects the fluid transfer device to the outlet port;
    a pressure sensor associated with the fluid path;
    a flow restrictor between the pressure sensor and the outlet port; and
    means for actuating the fluid transfer device in accordance with a delivery profile that includes a plurality of fluid transfer device actuations, determining based on pressure sensed only upstream of the flow restrictor whether an actual volume delivered during a fluid transfer device actuation is the predetermined volume, and adjusting the number of actuations in the delivery profile in response to the actual volume delivered differing from the predetermined volume.

13. An ambulatory infusion device as claimed in claim 12, wherein
    the fluid transfer device includes an electromagnet pump that creates a pressure spike.

14. An ambulatory infusion device as claimed in claim 13, wherein
    the electromagnet pump comprises a fixed displacement electromagnet pump.

15. An ambulatory infusion device as claimed in claim 12, wherein
    the pressure sensor includes compliant diaphragm with a compliance value.

16. An ambulatory infusion device as claimed in claim 12, wherein
    adjusting the number of actuations in the delivery profile comprises adding an actuation equivalent of an over-delivery volume to a feedback accumulator in response to the actual volume delivered being greater than the predetermined volume.

17. An ambulatory infusion device as claimed in claim 16, wherein
    adjusting the number of actuations in the delivery profile comprises subtracting an actuation equivalent of an under-delivery volume from the feedback accumulator in response to the actual volume delivered being less than the predetermined volume.

* * * * *